United States Patent [19]

McCurry, Jr. et al.

[11] Patent Number: 4,950,743
[45] Date of Patent: Aug. 21, 1990

[54] PROCESS FOR PREPARATION OF ALKYLGLYCOSIDES

[75] Inventors: Patrick M. McCurry, Jr.; Carl E. Pickens, both of Decatur, Ill.

[73] Assignee: Henkel Kommanditgesellschaft auf Aktien, Duesseldorf, Fed. Rep. of Germany

[21] Appl. No.: 79,195

[22] Filed: Jul. 29, 1987

[51] Int. Cl.$^5$ .................... C07H 1/00; C07H 15/04; C07G 3/00

[52] U.S. Cl. .................... 536/18.6; 536/4.1; 536/18.5; 536/124

[58] Field of Search .................... 536/18.5, 18.6, 124, 536/4.1

[56] References Cited

U.S. PATENT DOCUMENTS

| | | | |
|---|---|---|---|
| 1,951,784 | 3/1934 | Bertsch | 252/353 |
| 2,049,758 | 8/1936 | Bertsch et al | 536/18.6 |
| 2,235,783 | 3/1941 | White | 536/18.5 |
| 2,275,969 | 3/1942 | Kongstad | 536/18.6 |
| 2,356,565 | 8/1944 | Chwaza | 536/18.6 |
| 2,374,236 | 4/1945 | Salzberg et al. | 536/18.6 |
| 2,390,507 | 12/1945 | Cantor | 536/18.6 |
| 2,422,328 | 6/1947 | Young | 536/4.1 |
| 2,609,367 | 9/1952 | Gaver et al. | 54/77 |
| 2,671,780 | 3/1954 | Gaver et al. | 536/111 |
| 2,671,781 | 3/1954 | Gaver et al. | 536/111 |
| 2,719,179 | 9/1955 | Mora | 536/1.1 |
| 2,862,913 | 12/1958 | Lynn, Jr. et al. | 526/200 |
| 2,867,651 | 1/1959 | Wise | 560/98 |
| 2,886,438 | 5/1959 | Barsky et al. | 426/554 |
| 2,956,963 | 10/1960 | Baird | 536/4.1 |
| 2,959,500 | 11/1960 | Schlapfer et al. | 127/37 |
| 2,974,134 | 3/1961 | Pollitzer | 269/45 |
| 3,073,788 | 1/1963 | Hostetter et al. | 521/175 |
| 3,092,618 | 6/1963 | Rosen | 536/103 |
| 3,157,634 | 11/1964 | Druey | 536/4.1 |
| 3,219,656 | 11/1965 | Boettner | 536/18.3 |
| 3,251,827 | 5/1966 | Schnell et al. | 536/119 |
| 3,305,535 | 2/1967 | Merten et al. | 527/302 |
| 3,314,493 | 4/1967 | Ames | 536/120 |
| 3,324,108 | 6/1967 | Moller | 536/120 |
| 3,346,558 | 10/1967 | Roth | 536/18.6 |
| 3,375,243 | 3/1968 | Nevin et al. | 536/18.6 |
| 3,450,690 | 6/1969 | Gibbons et al. | 536/18.5 |
| 3,480,616 | 11/1969 | Osipow | 536/119 |
| 3,547,828 | 12/1970 | Mansfield et al. | 252/351 |
| 3,598,865 | 8/1971 | Lew | 536/4.1 |
| 3,640,998 | 2/1972 | Mansfield et al. | 536/18.3 |
| 3,644,333 | 2/1972 | Osipow et al. | 536/119 |
| 3,653,095 | 4/1972 | Dupre et al. | 422/13 |
| 3,707,535 | 12/1972 | Lew | 536/18.6 |
| 3,721,633 | 3/1973 | Ranauto | 252/527 |
| 3,737,426 | 6/1973 | Throckmorton et al. | 414/424 |
| 3,766,165 | 10/1973 | Rennhard | 536/119 |
| 3,772,269 | 11/1973 | Lew | 536/4.1 |
| 3,839,318 | 10/1974 | Mansfield | 536/18.6 |
| 3,865,628 | 2/1975 | Callahan et al. | 34/2 |
| 3,865,880 | 2/1975 | Quelly et al. | 252/364 |
| 3,974,138 | 8/1976 | Lew | 536/18.6 |
| 3,994,827 | 11/1976 | Sakai et al. | 238/41 |
| 4,011,389 | 3/1977 | Langdon | 536/4.1 |
| 4,014,808 | 3/1977 | Herpers, Jr. et al. | 252/135 |
| 4,154,706 | 5/1979 | Kenkare et al. | 252/547 |
| 4,196,201 | 4/1980 | Boelle et al. | 514/25 |
| 4,223,129 | 9/1980 | Roth et al. | 536/18.6 |
| 4,224,411 | 9/1980 | Chibata et al. | 435/177 |
| 4,230,592 | 10/1980 | Miller et al. | 252/156 |
| 4,240,921 | 12/1980 | Kaniecki | 252/156 |
| 4,349,669 | 9/1982 | Klahr et al. | 536/127 |
| 4,393,203 | 7/1983 | Mao et al. | 536/124 |
| 4,456,586 | 6/1984 | Vanlerberghe et al. | 424/70 |
| 4,465,828 | 8/1984 | Rau et al. | 536/18.6 |
| 4,472,170 | 2/1984 | Hellyer | 44/51 |
| 4,483,779 | 11/1984 | Llenado et al. | 252/135 |
| 4,483,780 | 11/1984 | Llenado et al. | 252/135 |
| 4,483,979 | 11/1984 | Mao | 536/18.6 |
| 4,507,472 | 3/1985 | Usher et al. | 536/51 |
| 4,510,306 | 4/1985 | Langdon | 536/127 |
| 4,528,106 | 7/1985 | Grolitzer | 252/8.554 |
| 4,565,647 | 1/1986 | Llenado et al. | 252/354 |
| 4,609,478 | 9/1986 | Egan | 252/8.554 |
| 4,683,297 | 7/1987 | Vanami et al. | 536/18.6 |
| 4,704,453 | 11/1987 | Lorenz et al. | 536/18.6 |
| 4,713,447 | 12/1987 | Letton | 536/18.6 |
| 4,721,780 | 1/1988 | McDaniel, Jr. et al. | 536/18.6 |

OTHER PUBLICATIONS

Abdel-Akher et al.; "The Reduction of Sugars with Sodium Borohydride", 73:4691–4692, Oct. 1951.
Herman; Soaps/Cosmetics/Chemical Specialities 54:48–49, Jun. 1978.
Noller et al.; J.A.C.S. 60:2076–2077, (1938).
Kirk and Othmer; *Encyclopedia of Chemical Technology* vol. 7, (1951) pp. 269–271.
Gorin et al.; Can. J. Chem. 39: 2474–2485 (1961).
Stanek et al.; *The Monosaccharides* pp. 256–258 (1963).
Schram et al.; Nature 197: 1074–1076 Mar. 1963.
Wing et al.; Carbohydrate Research 10: 441–448 (1969).
Hughes et al.; J. Amer. Oil Chem. Soc. 47(5): 162–167 May 1970.
Brown et al.; Can. J. Chem. 48(16): 2525–2531 Aug. 1970.
Pigman et al.; *The Carbohydrates* pp. 281–283, Second Edition (1972).
Grip et al.; Chem. Phys. Lipids 23: 321–325 (1979).

*Primary Examiner*—Ronald W. Griffin
*Assistant Examiner*—Nancy S. Carson
*Attorney, Agent, or Firm*—Ernest G. Szoke; Wayne C. Jaeschke; Daniel S. Ortiz

[57] ABSTRACT

A process for preparing alkylglycosides by reacting an 8 to 20 carbon atom monohydric alcohol with a monosaccharide in the presence of an acid catalyst, while under partial vacuum, followed by neutralizing the reactant product with an alkaline metal hydroxide in an amount about equal on a molar basis to the amount of catalyst, and removal of the residual unreacted alcohol.

11 Claims, No Drawings

PROCESS FOR PREPARATION OF ALKYLGLYCOSIDES

BACKGROUND OF THE INVENTION

The present invention relates to a process for making alkylglycosides. In particular, it relates to a process for making a light straw colored, i.e., substantially colorless, alkylglycoside product.

Alkylglycosides are nonionic surfactants which provide detergency, foaming, emulsifying, and wetting properties comparable to those of other nonionic surfactants. For a number of years it has been proposed to use alkylglycosides as surfactants either alone or in combination with other anionic or nonionic surfactants in detergent formulations.

Despite the long recognized potential uses for alkylglycosides in detergents, they have been primarily relegated to use in industrial detergency applications. The reason for this is that presently available economical processes for making alkylglycosides produce a product having a substantial amount of color producing impurities, resulting in a dark, coffee-colored product.

Although the color of the alkylglycoside product may be of little importance in some industrial detergent applications, color is crucial for many other industrial applications and, as a practical matter, for all household detergent applications. The reason for this is simply that, as a general rule, those using such products do not wish to wash their clothes and dishes with a coffee-colored detergent product.

To enable the use of alkylglycosides in household detergent formulations, there has been a need for a simple and economical process for making a substantially colorless, e.g., a light straw colored, alkylglycoside product. The present invention provides for such a process.

SUMMARY OF THE INVENTION

The present invention provides for a process for making a substantially colorless alkylglycoside product which includes the steps of:

(1) admixing a compound selected from the group consisting of monosaccharides, and compounds hydrolyzable to monosaccharides, with a monohydric alcohol containing 8 to 20 carbon atoms;

(2) reducing the pressure to a pressure sufficient to remove a substantial amount of any more volatile reaction by-products resulting from the reaction between the alcohol and the monosaccharide;

(3) heating the resulting alcohol, monosaccharide mixture to a temperature sufficient to enable them to react to produce an alkylglycoside;

(4) adding a sufficient amount of an acid catalyst, capable of subsequently being completely neutralized with stoichiometric amounts of an alkaline substance such that the mixture will not have excessive acidity or alkalinity, to effect reaction between the alcohol and the monosaccharide to produce an alkylglycoside; and (5) adding a sufficient amount of an alkaline substance to neutralize the catalyst.

The process preferably includes the step of removing substantially all of the unreacted alcohol.

DETAILED DESCRIPTION OF SPECIFIC EMBODIMENTS

In the process of the present invention, the monohydric alcohols having from 8 to 20 carbon atoms may be primary or secondary alcohols, straight or branch chained, saturated or unsaturated, alkyl or aralkyl alcohols, ether alcohols, cyclic alcohols, or heterocyclic alcohols. A preferred group of monohydric alcohols are those having the formula ROH where R is an alkyl group having from 8 to 16 carbon atoms.

The monosaccharides of the present invention are the hexoses and pentoses. Typical examples include glucose (dextrose), mannose, galactose, talose, allose, altrose, idose, arabinose, xylose, lyxose, ribose, and the like. Other examples include the monohydrate forms of these compounds. The preferred monosaccharide is glucose monohydrate due to its availability and low cost. Compounds hydrolyzable to monosaccharides may also be employed, such as starch, maltose, sucrose, lactose, melibiose, raffinose, methyl glucosides, butyl glucosides, anhydro sugars such as levoglucosan, 1,6- anhydroglucofuranose, and the like.

The molar ratio of high molecular weight alcohol to monosaccharide is suitably between about 1.5 to about 10, and preferably between about 2.5 to about 6.0.

The particular molar ratio chosen depends upon the desired average degree of polymerization (DP) of the monosaccharide onto the alcohol. The DP represents the average number of monosaccharide derived moieties that are attached to each alkyl chain of the alkylglycosides produced. Generally, as the alcohol to monosaccharide ratio is increased, the DP decreases. Likewise, as this ratio is decreased, the DP increases. Mathematically $$,31$$

where f equals 5 for glucose and is the number of hydroxyls on the sugar ring in the cyclic acetal form, empirically R varies between about 1.5 –2.5 and is the glucose binding reactivity of the fatty alcohol relative to the average reactivity of available non-anomeric hydroxyl groups of the sugar moiety and $F_T$ is the mole ratio of alcohol to available carbohydrate.

Preferably, the ratio of alcohol to monosaccharide will be chosen to allow the production of an alkylglycoside product having a DP between about 1.2 and 2.2.

Low alcohol to monosaccharide ratios, i.e., ratios less than about 1.5, should be avoided for optimized reaction control. This is because under these conditions two irreversible and undesirable side reactions may take place. For example, when glucose is used as the monosaccharide, elevated levels of glucose polymers (polydextrose) may form, especially during the latter stages of the reaction. This results in excessive foaming and in the loss of glucose in the reaction material, actually causing an increase in $F_T$ (the alcohol to glucose ratio) and hence a decrease in DP. The second reaction involves the dehydration of glucose into hydroxy methyl furfural (HMF) and related condensation products (e.g., polyanhydro HMF). These substances are, or later yield, color bodies which would contaminate the product, preventing the further process steps of the present process from producing a substantially colorless alkylglycoside product.

With glucose as the carbohydrate, the temperature for carrying out the reaction may vary between about 85° C. and about 120° C., preferably between about 95° C. and about 110° C. If a temperature significantly greater than 120° C. is used, the side reactions increase faster than the primary reaction. When glucose is used, this causes an increase in polydextrose formation and unwanted color bodies.

The temperature also should not be significantly below 85° C. This is because such a reduced temperature would cause an unacceptable reduction in reaction rate.

The reaction must take place in an environment which facilitates the removal of more volatile reaction byproducts. This environment may be conveniently maintained by reducing the pressure under which the reaction occurs. This reduction of pressure enables any more volatile reaction by-products to be evaporated from the reaction mixture. Preferably, such a reduction in pressure is achieved by applying a vacuum to the reaction system.

Preferred apparatus for applying vacuum to the reaction system includes steam jets or mechanical vacuum pumps. With higher fatty alcohols the final vacuum preferably should be applied at a pressure between about 20 mm Hg and about 100 mm Hg. This is especially desirable when water is a reaction by-product. If the absolute pressure is allowed to exceed 100 mm Hg to a significant extent, the water produced in the reaction between the alcohol and the monosaccharide may not be removed to the extent required to prevent the buildup of a separate water phase in the reaction system, which could cause the production of unacceptable amounts of polydextrose, when glucose is used as the monosaccharide, or retard the reaction due to its reversible nature.

If the pressure is kept significantly below 20 mm Hg, codistillation of lower alcohols may result. In addition, almost all of the water remaining in the reaction system could be evaporated. Under these circumstances, saccharide moieties, such as glucose, degrade faster, and their degradation products more rapidly form unacceptable levels of color bodies. An additional problem with vacuums below 30 mm is the inability to economically condense water vapor and the associated problems of high volumes of non-condensed vapors or contamination of vacuum pump fluids.

The acid catalyst employed in the present invention is used in an amount between about 0.05% and about 5, preferably between about 0.5% and about 2.0%, based upon the amount of monosaccharide used, on a molar basis. As with temperature, the catalyst concentration must be controlled to minimize the formation of color bodies and polydextrose when glucose is the chosen monosaccharide.

It is critical that a catalyst that may be easily neutralized with an alkaline substance, after the monosaccharide/alcohol reaction has terminated, be used to effect termination of the reaction of the present process. Otherwise, the resulting isolated product could include an unacceptable amount of color bodies, preventing the production of a substantially colorless alkylglycoside product. An aliphatic or aromatic, mono-sulfonic acid catalyst, for example, a toluene sulfonic acid catalyst, has been found suitable for the process of the present invention. Other commercially available catalysts like methane sulfonic acid, benzene sulfonic acid or lower alkyl substituted sulfonic acids like xylene or cumene sulfonic acids may also be suitable.

To neutralize the catalyst, an alkaline substance, preferably an alkali metal hydroxide such as sodium hydroxide, is used in an amount about equal, on a stoichiometric basis, to the amount of material needed to neutralize the catalyst. If a toluene sulfonic acid catalyst is used, one mole of the alkaline substance may, for example, react with one mole of catalyst. If one mole of the alkaline substance reacts with one mole of the catalyst, for example when sodium hydroxide is used to neutralize the catalyst, then an amount of the alkaline material about equal to the amount of catalyst, on a molar basis, is used to neutralize the catalyst. Such a neutralization reaction would yield one mole of neutral sodium toluene sulfonate for each mole of catalyst and alkaline substance used.

It should be appreciated that when other acid catalysts are used —such as sulfuric acid —they may not be easily neutralized. The inability to determine and control neutrality with such a catalyst could cause the production of an alkylglycoside product having an unacceptable color for household detergent uses.

For example, sulfuric acid forms esters with the alcohol, the alkylglycosides and the saccharides present. These esters themselves may cause the production of color bodies. Just as important, because the amount of these esters may be variable and difficult to determine, it may be nearly impossible to calculate the amount of alkaline material needed to neutralize the sulfuric acid and its half acid esters present and to maintain neutrality during a subsequent isolation step.

If too much alkaline material is used —such as when stoichiometric amounts of a basic compound are applied to a sulfuric acid catalyzed product —then the excess alkalinity could cause monosaccharide degradation, forming base catalyzed and promoted reactions and volatile and non-volatile color bodies. Similarly, if insufficient alkaline material is added, then acid catalyzed side reactions may cause the production of color bodies during handling and/or undesired polymerization of the resulting product during isolation.

For lowest colored products, it is desirable to maintain a certain minimum level of water in the reaction mixture at all times. For example, when glucose monohydrate is the starting material, this water retention helps solubilize the glucose, prevents the degradation of the monosaccharide, which could otherwise accelerate, and slows down color body forming condensation. In conjunction with maintaining the vacuum pressure within a specified range, it has been found that use of glucose monohydrate as the monosaccharide starting material helps ensure that a preferred amount of water will be present in the mixture at the time the reaction is started.

When glucose monohydrate is used as the monosaccharide that is combined with the alcohol, vacuum is applied at a pressure between about 20 mm Hg and about 100 mm Hg, preferably between about 30 mm Hg and about 60 mm Hg. This material cannot be heated or reacted directly with the higher alcohols in the presence of the acid catalyst because of the large amount of water initially present in the mixture. The presence of this combination of water and acid could cause the production of unwanted by-products —in particular melted and/or agglomerated dextrose or polydextrose —or could retard the reaction because of its reversibility.

To remove the excess water, the mixture is heated, in the absence of acid, for between about 0.5 and about 2 hours, until most of the water of hydration is evaporated. The temperature applied to evaporate the water preferably is between about 60° C. and about 70° C. Although most of the water is removed by evaporation, thus ensuring that agglomerated dextrose formation will not occur, enough water is retained in the mixture, such as between 0.1% and 0.25% based upon the weight of the reaction mixture, to ensure that later glucose degradation and polymerization of dehydration products is minimized.

The mixture is then heated to a temperature preferably between about 90° C. and about 120° C., over a period of between about 0.5 and about 1.5 hours. The catalyst is then added to start the reaction. After the reaction begins, the water produced is eventually balanced by the water removed by evaporation. When this steady state is reached, enough water remains in the reaction mixture to inhibit glucose degradation and polymerization of dehydration products.

If anhydrous glucose is used instead of glucose monohydrate as the monosaccharide starting material, there will be little water in the mixture, before the reaction begins. After the reaction begins, water will gradually build up in the reaction mixture until the water produced becomes balanced by the water evaporated. At this time, the reaction mixture includes enough water, probably about 0.1% based upon the weight of the reaction mixture or less, to inhibit glucose degradation.

It should be appreciated that the actual amount of water present in the reaction mixture as the reaction takes place depends upon the pressure, type of alcohol used, the temperature applied and may also depend upon the monosaccharide starting material.

It should also be appreciated that when glucose monohydrate is used as the monosaccharide starting material, instead of anhydrous glucose, the amount of water required to prevent or minimize glucose degradation is present in the mixture prior to the beginning of the reaction; whereas when anhydrous glucose is the monosaccharide starting material, the amount of water needed to help solubilize glucose and prevent or minimize glucose degradation may not be generated until after the reaction has proceeded for a period of time.

When glucose or glucose monohydrate is used as the monosaccharide starting material, it has been found that an acceptable product may also be produced without having to allow the reaction to proceed until substantially all of the glucose has reacted. As an alternative to allowing the reaction to progress to completion, which for a glucose/ 8 to 18 carbon straight chain alcohol blend may require from about 2 to about 10 hours, one may choose to allow the reaction to proceed until, for example, about 0.1% to about 3% of the glucose starting material remains. The time needed to achieve this extent of reaction would be from about 1.5 to about 6 hours when an 8 to 18 carbon straight chain alcohol is blended with the glucose. The advantage from shortening the reaction time is that the less time the reaction proceeds, the more kinetically controlled the process and the lesser the amount of undesirable by-products produced.

To ensure that the remaining glucose will not react to produce unwanted by-products, an amount of NaBH$_4$ (sodium borohydride) may be added. Functionally, the NaBH$_4$ reduces the excess glucose to sorbitol, and other reducing sugars to their corresponding alditols. Preferably at least about 1 gram of NaBH$_4$ is added for every 10 to 20 grams of excess glucose. Using NaBH$_4$ to hydrogenate the excess glucose has been found in some cases to be more efficient than to bleach the product that would otherwise result if the glucose had not been converted to sorbitol.

In ascertaining and/or quantifying the color (e.g., the relative darkness or lightness) characteristics of aqueous glycoside solutions, such as are produced in the process of the present invention, it is convenient to utilize the extinction coefficient of the glycoside material of interest using a suitable spectrophotometer (e.g., a Spectronic 20) over a path length of 1 cm and using 470nm wavelength light. Since the extinction coefficient is essentially a measure of the ability of the glycoside solution of concern to absorb light as opposed to transmitting same, small extinction coefficients correspond to substantially colorless glycoside solutions. Accordingly, the process of the present invention has the effect of producing an alkylglycoside product having a reduced extinction coefficient.

The term "extinction coefficient" as used herein refers to the calculated absorbance of a theoretical solution containing one gram of solid material per cm$^3$ of solution measured as described above and calculated according to the following formula:

,33

While not being a required or overriding feature or parameter of the present invention, it can be stated as a general point of reference that dark colored glycoside solutions, such as are produced in other processes for making an alkylglycoside product, can have extinction coefficients of over 20, whereas the extinction coefficient of the alkylglycoside product made in the present invention is generally less than 2.5, and more typically less than 1.0.

As an alternative to the use of glucose monohydrate as the starting material in the process of the present invention, a butyl glycoside/glucose mixture may be used as the monosaccharide starting material. Such a mixture may be made by admixing butanol with glucose, preferably in a butanol to glucose molar ratio of about 2.5 to about 8.0. When glucose monohydrate is used as the monosaccharide that is combined with butanol, vacuum is applied at a pressure between about 100 mm Hg and about 300 mm Hg, preferably between about 125 mm Hg and about 285 Hg. To remove a portion of the water of hydration initially present in the mixture, the mixture is heated for between about 0.5 and about 2.0 hours. The temperature applied to distill the water is preferably between about 60° C. and about 90° C. About 0.2% to about 2.0% water, based on the total weight of the mixture, remains in the mixture. Both water and butanol are removed by distillation under these conditions. The distilled butanol may be returned to the mixture after dehydration, preferably by distillation.

The pressure may then be increased to between about 450 mm Hg to about 750 mm Hg. The mixture is then heated over a period of between about 0.5 hours to about 1.5 hours to a temperature between about 100° C. and about 115° C. An acid catalyst that may be completely neutralized with stoichiometric amounts of an alkaline substance is added in an amount between about 0.5% and about 2.0%, based on the amount of glucose used, on a molar basis. The reaction will produce a butyl glycoside product and a water by-product. The reaction should be continued until the dextrose has dissolved. This should require approximately 1 to 5 hours. During this period, both water and butanol are removed by distillation. The distilled butanol may be returned to the reaction mixture after dehydration, preferably by distillation.

Alternatively, a butyl glycoside/glucose mixture may be made by admixing butanol with anhydrous glucose or glucose monohydrate, preferably in a butanol to glucose molar ratio of about 2.5 to about 8.0, along with an acid catalyst that may be completely neutralized with stoichiometric amounts of an alkaline substance. Because of the water of hydration initially present in the mixture when glucose monohydrate is used, and because the reaction will produce a butyl glucoside product and a water by-product, the pressure must be reduced to a level sufficient to enable removal of a substantial amount of water. The pressure applied will allow about 0.2% to 2.0% water, based upon the total weight of the reaction mixture, to remain in the mixture, and preferably should be between about 450 mm Hg to about 750 mm Hg. The catalyst should be added in an amount between about 0.5% and about 2.0% based on the amount of glucose used, on a molar basis.

After the butanol, glucose, and catalyst have been combined and the pressure reduced, the mixture is heated to a temperature between about 100° C. and about 115° C., to enable the butanol to react with the glucose. The reaction should be continued until the dextrose has dissolved. This should require approximately 1 to 6 hours. During this period, both water and butanol are removed by distillation. The distilled butanol may be returned to the reaction mixture after dehydration, preferably by distillation.

Once the glucose has dissolved, this butyl glycoside/glucose mixture, which makes up the starting material for the process described in this embodiment, should contain between about 24% and 50% butyl glycosides, between about 1% and about 5% glucose, and between about 45% and 75% butanol. To this mixture may then be added a monohydric alcohol containing 8 –20 carbons. This 8 –20 carbon monohydric alcohol replaces the butanol as it is being distilled from the reaction mixture. The ratio of alcohol to the glucose, that was admixed with the butanol, is about 2.5 to about 6 on a molar basis. During this step in the process the pressure is preferably reduced to in the process the pressure is preferably reduced to between about 20 mm Hg and about 100 mm Hg at a relatively constant rate over a period of between about 1.5 to about 4 hours. This enables the removal of a substantial amount of the butanol from the reaction mixture. After the 8 –20 carbon alcohol is added, the reaction preferably proceeds for an additional 0.5 to 6 hours. After this period of time, the residual butanol should have been reduced to between about 1% and about 2.5% of the reaction mixture, by weight, and the residual butyl glucosides (on a dry solids basis) should have been reduced to between about 2% and about 8% of the reaction mixture, by weight. At this point in the process, a sufficient amount of an alkaline substance, preferably sodium hydroxide, is added to neutralize the catalyst. The residual unreacted alcohol is then removed from the reaction mixture through evaporation or some equivalent means. The resulting product should contain between about 80% and about 95% alkylglycosides, about 2% and about 13% polydextrose, about 1% and about 3% nonpolar by-products, and about 2% and about 8% butyl glucosides.

The following examples illustrate some of the advantages of the present invention.

EXAMPLE 1

To a 2-liter, four-neck flask equipped with an overhead stirrer, thermometer and addition funnel, was added 732.5 grams (5.0 moles) of a commercially available mixture comprised of about 44 parts of n-octanol, 55 parts of n-decanol and some n-hexanol and n-dodecanol. Stirring was started and 396 grams (2.0 moles) of glucose monohydrate was added. Vacuum was applied and the pressure was reduced to about 50 mm Hg. The mixture was then heated for about 0.5 to 2 hours until most of the water of hydration was evaporated, while the pot temperature was about 60° C. to 65° C. The mixture was then heated until it reached about 100° C. At this point, 35 ml water and 2 ml alcohol were collected. At this point in the process, it is estimated that the reaction mixture retained about 0.18% water, as measured by a Karl Fischer titration, based upon the weight of the total mixture. Then 3.80 grams (0.020 moles) of p-toluene sulfonic acid monohydrate catalyst was added as a 50% solution (7.60 grams) in wet 8 –10 carbon alcohol (1.52 grams $H_2O$ and 2.28 grams alcohol). During the next 4 to 5 hours, distillate was collected which was comprised of about 36 ml of a lower water layer and about 4 ml of an upper or wet alcohol layer. The resulting mixture was hazy, but free of dense insolubles. The yellowish reaction mixture was found to contain less than about 0.1% reducing sugars.

To this mixture was then added 1.60 grams (0.020 moles) of a 50% aqueous solution of sodium hydroxide. Ten minutes later an aliquot of 2.17 grams of reaction mixture was diluted to 10 ml with 1:1 isopropyl alcohol (IPA): water (1.0 gram dry solids/10 ml). This solution was found to have a pH of about 7.0. A reverse phase chromatographic analysis showed that the reaction mixture itself contained 53.8% alcohol and 21.5% monoglucosides. Evaporation of the fatty alcohol using a Leybold Heraeus thin film evaporator, using an oil temperature of about 165° C. and a pressure of about 1 mm Hg, produced a straw yellow residue. This residue, in dry solid form, consisted of about 0.8% sodium tosylate, about 3.3% polydextrose, about 2.0% nonpolar reaction by-products, and about 93.9% 8 –10 carbon alkylglucosides. The DP of the alkylglucosides, using NMR, liquid chromatography, and gas chromatography methods, was calculated to be about 1.65. When dissolved in water (70% dry solids) the solution became a crystal clear light amber solution.

Using a Spectronic 20 (Bausch and Lomb) at 470nm, this solution was found to have an extinction coefficient of about 0.6.

EXAMPLE 2

To a 4-liter, four-neck flask equipped with an overhead stirrer, thermometer and addition funnel, was added 2328 grams (12.0 moles) of a commercially available mixture, i.e., Neodol 23 (Shell Oil Co.), which was comprised of about 43 parts n- and branched 12 carbon alcohols, 55 parts of n- and branched 13 carbon alcohols, and smaller amounts of 11, 14 and 15 carbon alcohols. Stirring was started and 396 grams (2.0 moles) of glucose monohydrate was added. Vacuum was applied and the pressure was reduced to about 50 mm Hg. The mixture was then heated for about 0.5 to 2 hours until most of the water of hydration was evaporated, while the pot temperature was about 60° C. to 65° C. The mixture was then heated until it reached about 105° C. At this point, 35 ml water and 0.1 ml alcohol were collected. At this point in the process, the reaction mixture retained about 0.13% water, based upon the weight of the total mixture. Next, 3.80 grams (0.020 moles) of p-toluene sulfonic acid monohydrate catalyst was added as a 50% solution (7.60 grams) in wet Neodol 23 alcohol (1.52 grams $H_2O$ and 2.28 grams alcohol). During the next 8 to 9 hours, distillate was collected which was comprised of about 36 ml of a lower water layer and about 4 ml of an upper or wet alcohol layer. The resulting reaction mixture was hazy, but free of dense insolubles. The yellowish reaction mixture was found to contain less than about 0.1% reducing sugars and less than 0.1% water.

To this mixture was then added 1.60 grams (0.020 moles) of a 50% solution of sodium hydroxide in water. Ten minutes later an aliquot of 4.5 grams of reaction mixture was diluted to 10 ml with 60:40 $IPA:H_2O$ (1.0 gram dry solids/10 ml). This solution was found to have a pH of about 6.9. A reverse phase chromatographic analysis showed that the crude reaction mixture contained 78% alcohol and 14.1% monoglucosides. Evaporation of the fatty alcohol using a Leybold Heraeus thin film evaporator, using an oil temperature of 205° C. and a pressure of about 1 mm Hg, produced a straw yellow residue. This residue, in dry solid form, consisted of about 0.7% sodium tosylate, about 3.0% polydextrose, about 2.0% nonpolar reaction by-products, and about 94.3% alkylglucosides. The average degree of polymerization of the alkylglucosides, using NMR, liquid chromatography and gas chromatography methods, was calculated to be about 1.32. When dissolved in water (60% dry solids) the solution became a crystal clear light amber solution.

Using a Spectronic 20 at 470nm, the solution was found to have an extinction coefficient of about 0.7.

The following Examples 3 and 4 may also be performed and should produce the following results.

EXAMPLE 3

To a 4-liter, four-neck flask equipped with an overhead stirrer, thermometer and addition funnel, was added 2134 grams (11 moles) of a commercially available mixture comprised of about 43 parts of n- and branched $C_{12}$ alcohol parts and 55 parts of n and branched $C_{13}$ alcohol, along with small amounts of $C_{11}$, $C_{14}$ and $C_{15}$ alcohols. Stirring was started and 396 grams (2 moles) of glucose monohydrate added. Vacuum was then applied and the pressure reduced to about 90 mm Hg. The mixture was then heated for about 0.5 to 2 hours until most of the water of hydration was evaporated, while the pot temperature was about 65° C to 70° C. The mixture was then heated until it reached about 105° C. At this point, 29 ml water and 0.2 ml alcohol was collected. At this point in the process, it is estimated that the reaction mixture retained about 0.25% water, based upon the weight of the total mixture. 3.80 grams (0.020 moles) of p-toluene sulfonic acid monohydrate catalyst was then added as a 50% solution (7.60 grams) in wet Neodol 23 (Shell Oil Co.) (1.52 grams $H_2O$ and 2.28 grams alcohol). During the next 9 -10 hours, distillate was collected which was comprised of about 36 ml of a lower water layer and about 3 ml of an upper or wet alcohol layer. The resulting mixture was hazy, but free of dense insolubles. The yellowish reaction mixture contained less than about 0.3% reducing sugars and about 0.3% water.

To this mixture was then added 1.60 grams (0.020 moles) of a 50% solution of sodium hydroxide in water. Ten minutes later a 4.2 gram aliquot of the reaction mixture was dissolved in 60/40 $IPA/H_2O$ (1.0 gram dry solids/10 ml). This mixture had a pH of about 6.8. A reverse phase chromatographic analysis of the reaction mixture showed that the mixture contained 76% alcohol and 13.6% monoglucosides. Evaporation of the fatty alcohol using a Leybold Heraeus thin film evaporator, using an oil temperature of 207° C. and a pressure of about 1 mm Hg, produced a straw yellow residue. This residue, in dry solid form, consisted of about 0.7% sodium tosylate, about 7% dextrose plus polydextrose, about 2% nonpolar reaction by-products, and about 90.3% alkylglucosides. The average degree of polymerization of the alkylglucosides, using NMR, liquid chromatography and gas chromatography methods, was about 1.35. When dissolved in water (60% dry solution) the solution became a crystal clear light amber solution.

Using a Spectronic 20 at 470nm, the solution had an extinction coefficient of about 0.5.

EXAMPLE 4

To a 1-liter, four-neck flask equipped with an overhead stirrer, thermometer and addition funnel, may be added 530 grams (7.15 moles) butanol. Stirring may be started and 230 grams (1.16 moles) of glucose monohydrate added. Vacuum may be applied and the pressure may be reduced to about 125 mm Hg. The mixture should then be heated at 70° C. for about 0.5 hours. 77 ml of wet butanol and 8 ml of water should be removed while an equal volume of dry butanol is added back to the mixture. The pressure should then be changed to 660 mm Hg and the mixture heated to 110° C. At this point in the process, it is expected that the mixture will retain about 0.8% water, based on the weight of the total mixture. 2.21 grams (0.0116 moles) of p-toluene sulfonic acid monohydrate catalyst should then be added as a 50% solution (4.42 grams) of wet butanol (0.22 grams water and 1.99 grams butanol). During the next 40 minutes, distillate should be collected which should be comprised of about 170 ml of wet butanol while an equal volume of dry butanol is added back to the reaction mixture. The resulting mixture should be yellowish and hazy, but free of dense insolubles. The resulting mixture should contain about 31% butyl glucosides, 3% glucose, 65% butanol, and 1% water. 557 grams (3.48 moles) of a commercially available mixture, i.e., Neodol 91 (Shell Oil Co.), which is comprised of about 1 part, n- and branched 8 carbon alcohols, 18 parts n- and branched 9 carbon alcohols, 46 parts of n- and branched 10 carbon alcohols, and 35 parts of n- and branched 11 carbon alcohols should be added uniformly over the next 3 hours. During this period, 685 ml of wet butanol should be uniformly removed by distillation by uniformly decreasing the pressure to 20 mm Hg. The reaction is continued at these conditions for an additional 1.5 hours during which time an additional 27 ml of distillate should be collected. The resulting mixture should be slightly hazy, but free of dense insolubles. The light brown reaction mixture should contain less than about 0.1% reducing sugars.

The mixture may then be neutralized by the addition of 0.928 grams of a 50% aqueous solution of sodium hydroxide (0.0116 moles). In order to determine the pH of the neutralized mixture, ten minutes later, a 2.6 gram aliquot (1.0 gram dry solids) of the reaction mixture may be diluted to 10.0 ml with 1:1 IPA:H$_2$O and the pH can be measured. The solution should have a pH of 6.8. A reverse phase chromatographic analysis should show that the mixture contains 62.8% alcohol and 20.0% monoglucosides. Evaporation of the fatty alcohol using a Leybold Heraeus thin film evaporator, using an oil temperature of 165° C. and a pressure of about 1 mm Hg, should produce a light brown residue. This residue, in dry solid form, should consist of about 0.7% sodium tosylate, about 7% polydextrose, about 2% nonpolar reaction by-products, about 7% butylglucosides, and about 83.3% 8–10 carbon alkylglucosides. The average degree of polymerization of the 8–10 carbon alkylglucosides, using previously described methods, should be calculated to be about 1.6. When dissolved in water (70% dry solution) the solution is expected to become a crystal clear light amber colored solution.

Using a Spectronic 20 at 470nm, the solution is expected to have an extinction coefficient of less than about 2.5.

EXAMPLE 5

For comparison purposes, a product was made following the process steps of Example 1, but using 2 moles anhydrous glucose, 5 moles alcohol and 40 mmoles of a sulfuric acid catalyst instead of the glucose monohydrate and p-toluene sulfonic acid monohydrate catalyst. Because anhydrous glucose was used in this example instead of glucose monohydrate, the reaction mixture was heated directly to about 100° C., without the initial pre-evaporation step that is needed to remove most of the water from the glucose monohydrate when that is the monosaccharide starting material.

Prior to neutralization with a stoichiometric amount of sodium hydroxide (80 mmoles) the SO$_3$ containing moieties in the reaction product included estimated:

| | |
|---|---|
| 22 mmoles | sulfuric acid, |
| 13.34 mmoles | alcohol sulfuric acid esters, |
| 3.24 mmoles | alkylglucoside sulfuric acid esters, |
| 1.42 mmoles | glucoside sulfuric acid esters; |

After neutralization, the sulfate containing moieties in the resulting product included approximately:

| | |
|---|---|
| 22 mmoles | sodium sulfate, |
| 13.34 mmoles | sodium alkylsulfates, |
| 3.24 mmoles | sodium alkylglucoside sulfates, |
| 1.42 mmoles | sodium sulfated glucose. |

Also included were about 18.0 mmoles sodium hydroxide.

In contrast to these reaction products, when the p-toluene sulfonic acid catalyst of Example 1 is used, in an amount of 20 mmoles, neutralization with 20 mmoles sodium hydroxide produces 20 mmoles sodium tosylate, without any esterified by-products, such as are produced when a sulfuric acid catalyst is used.

The composition of the final product of Example 5, after wiped film evaporation of the residual alcohol, was as follows:

| | |
|---|---|
| about 0.7% | sodium sulfate, |
| about 1.3% | sulfated glucose moieties and alcohols, |
| about 1.0% | sodium salts of carboxylic acids, |
| about 7.7% | polydextrose, |
| about 2.0% | nonpolar reaction by-products, and |
| about 87.3% | 8–10 carbon alkylglucosides. |

Using a Spectronic 20 at 470nm, this solution was found to have an extinction coefficient of over 20. This corresponds to a dark coffee color for the resulting product, in contract to the substantially colorless product such as is produced following the process shown in Example 1.

EXAMPLE 6

As an alternative to the process described in Example 1, the reaction may be allowed to proceed for 3 to 3.5 hours rather than for 4 to 5 hours. In this alternative process, the resulting mixture would include about 1.8% unreacted glucose. To this mixture should be added about one gram of NaBH$_4$ in aqueous NaOH. The NaBH$_4$ should reduce the unreacted glucose to sorbitol.

Following the isolation steps of Example 1, the resulting residue should, in dry solid form, consist of about 1.3% of a mixture of sodium tosylate and borate, about 6% of a mixture of sorbitol and polydextrose, about 2% nonpolar reaction by-products, and about 90.7% 8–10 carbon alkylglucosides. The average degree of polymerization of the alkylglucosides should be about 1.59. Like the Example 1 product, this product, when dissolved in water (70% dry solids), should produce a crystal clear light amber solution.

Using a Spectronic 20 at 470 nm, this solution should show an extinction coefficient of about 0.5.

Alternatively, the reaction mixture may be neutralized with NaOH and evaporated prior to the aqueous solution, which contains some of the unreacted glucose, being reduced with sodium borohydride. In this process, a significant portion of the glucose may be thermally dehydrated to anhydro glucose during wiped film evaporation. Addition of the sodium borohydride after the neutralization and evaporation steps should produce a caustic stable product.

Additional advantages and modifications will readily occur to those skilled in the art. The invention in its broader aspects is therefore not limited to the specific details, representative apparatus, and illustrative examples. It is apparent that the proportion of reactants, time of reaction, vacuum pressure, reaction temperature, and catalyst concentration may be varied, as may be the types of sugars, alcohols, and neutralizing agents. Accordingly, departures may be made from the described details without departing from the spirit or scope of the disclosed general inventive concept.

I claim:

1. A process for the preparation of alkylglycosides which comprises:

forming a mixture comprising at least one member selected from the group consisting of reducing monosaccharides and compositions hydrolyzable to reducing monosaccharides, at least one monohydric alcohol having from 8 to 20 carbon atoms and an acid catalyst for the reaction between the alcohol and the saccharide to produce an alkylglycoside;

heating the mixture at a temperature to react the alcohol with the saccharide under a reduced pressure, with removal of water formed by the reaction of the alcohol with the saccharide to form a reaction mixture; and adding a sufficient amount of a caustic alkali metal borohydride to the reaction mixture to neutralize the acid catalyst and reduce the unreacted saccharide.

2. A process of claim 1 for the preparation of alkylgylcosides which comprises:

admixing a compound selected from the group consisting of monosaccharides, and compounds hydrolyzable to monosaccharides, with a monohydric alcohol containing 8 to 20 carbon atoms;

reducing the pressure to a pressure sufficient to remove a substantial amount of any material more volatile than the alcohol;

heating the resulting alcohol, monosaccharide mixture to a temperature sufficient to enable them to react to produce an alkylglycoside;

adding a sufficient amount of an acid catalyst, capable of subsequently being completely neutralized with stoichiometric amounts of an alkaline substance such that the mixture will not have excessive acidity or alkalinity, and reacting the alcohol and the monosaccharide to produce an alkylglycoside; and adding a sufficient amount of a caustic sodium borohydride to neutralize the acid catalyst and reduce unreacted saccharide.

3. The process of claim 2 wherein the compound hydrolyzable to monosaccharides is glucose monohydrate and which further includes the steps of applying a vacuum at a sufficient pressure and applying heat to maintain a sufficient temperature to remove a substantial amount of the water of hydration from the glucose monodydrate prior to adding the acid catalyst and wherein the material more volatile than the alcohol is water.

4. The process of claim 2 further including the step of removing substantially all of the unreacted alcohol.

5. The process of claim 2 wherein the catalyst is an aromatic, mono-sulfonic acid catalyst, the ratio of alcohol to monosaccharide is between about 1.5 and about 10; the mixture is heated to a temperature between about 85° C. and about 120° C.; the pressure is reduced to a pressure between about 20 mm Hg and about 100 mm Hg; the catalyst is added in an amount between about 0.05% and about 5%, based upon the amount of moles of monosaccharide in the mixture; and the alkaline substance is added in an amount about equal, on a stoichiometric basis, to the amount required to neutralize the catalyst.

6. The process of claim 5 wherein the aromatic, monosulfonic acid catalyst is a toluene sulfonic acid catalyst and the alkaline substance is an alkali metal hydroxide that is added in an amount about equal, on a molar basis, to the amount of the catalyst.

7. The process of claim 6 wherein the ratio of alcohol to monosaccharide is between about 2.5 and about 6.0; the mixture is heated to a temperature between about 95° C. and about 110° C.; the pressure is reduced to a pressure between about 20 mm Hg and about 100 mm Hg; the catalyst is added in an amount between about 0.5% and about 2.0%, based upon the amount of moles of monosaccharide in the mixture; the alkaline substance is selected from the group consisting of sodium and potassium hydroxide and is added in an amount about equal, on a molar basis, to the amount of catalyst.

8. The process of claim 3 wherein the pressure applied to the glucose monohydrate, alcohol mixture prior to the addition of the catalyst is between about 30 mm Hg and about 60 mm Hg, and the mixture is heated at a temperature between about 60° C. and about 70° C. for about 0.5 to about 2 hours to evaporate a substantial amount of water, after which the temperature is raised to between about 90° C. and about 120° C., prior to the addition of the catalyst.

9. The process of claim 8 wherein the amount of water present in the reaction mixture prior to the addition of the catalyst is between about 0.1% and about 0.25%, based upon the weight of the total mixture.

10. The process of claim 2 wherein the monosaccharide is glucose and wherein the glucose is allowed to react with the alcohol for about 1.5 to about 6 hours.

11. The process of claim 10 wherein the amount of unreacted glucose is about 0.1% to about 3% based upon the amount of glucose originally added and wherein at least about 1 gram of sodium borohydride is added to each 10 to 20 grams of unreacted glucose to reduce the glucose to sorbitol.

* * * * *

UNITED STATES PATENT AND TRADEMARK OFFICE
CERTIFICATE OF CORRECTION

PATENT NO. : 4,950,743

DATED : August 21, 1990

INVENTOR(S) : Patrick M. McCurry, Jr. et al.

It is certified that error appears in the above-identified patent and that said Letters Patent is hereby corrected as shown below:

At Column 2, line 37, for ",31" read --$DP = 1 + (f-1)/(R*F_T)$,--.

Signed and Sealed this

Fifth Day of May, 1992

*Attest:*

DOUGLAS B. COMER

*Attesting Officer*      *Acting Commissioner of Patents and Trademarks*